US010189729B2

(12) United States Patent
Maghas et al.

(10) Patent No.: US 10,189,729 B2
(45) Date of Patent: Jan. 29, 2019

(54) METHOD AND APPARATUS FOR PREVENTING MOLD GROWTH IN THE RESERVOIR OF A FOOD WASTE RECYCLING APPLIANCE

(71) Applicant: Whirlpool Corporation, Benton Harbor, MI (US)

(72) Inventors: Rachel Maghas, Benton Harbor, MI (US); Bruce M. Jarnot, Benton Harbor, MI (US)

(73) Assignee: Whirlpool Corporation, Benton Harbor, MI (US)

( * ) Notice: Subject to any disclaimer, the term of this patent is extended or adjusted under 35 U.S.C. 154(b) by 233 days.

(21) Appl. No.: 15/245,292

(22) Filed: Aug. 24, 2016

(65) Prior Publication Data

US 2018/0057374 A1 Mar. 1, 2018

(51) Int. Cl.
*A47L 15/42* (2006.01)
*A61L 2/232* (2006.01)
(Continued)

(52) U.S. Cl.
CPC .......... *C02F 1/505* (2013.01); *A47L 15/4204* (2013.01); *A47L 15/4236* (2013.01); *A61L 2/232* (2013.01); *A61L 2/238* (2013.01); *B65F 7/00* (2013.01); *C05F 7/00* (2013.01); *C05F 9/02* (2013.01); *A47L 15/4208* (2013.01); *B02C 18/0084* (2013.01); *B02C 18/062* (2013.01); *B02C 23/08* (2013.01); *B02C 23/14* (2013.01); *B65F 2250/11* (2013.01); *C02F 2303/02* (2013.01); *C02F 2303/04* (2013.01);
(Continued)

(58) Field of Classification Search
CPC ............. A47L 15/4204; A47L 15/4208; A47L 15/4236; B65F 7/00; B65F 2250/11; C02F 1/505; C02F 2303/04; C02F 2307/12; C02F 2303/02; C02F 2303/20; A61L 2/232; A61L 2/238; B02C 18/0084; B02C 18/062; B02C 23/08; B02C 23/14; C05F 7/00; C05F 9/02; C05F 17/00; C05F 17/02
See application file for complete search history.

(56) References Cited

U.S. PATENT DOCUMENTS 4,836,230 A * 6/1989 Elliott ................. A47L 15/0089
134/138
5,198,118 A * 3/1993 Heskett ................... C02F 1/705
210/638
(Continued)

FOREIGN PATENT DOCUMENTS

DE 4031664 A1 4/1992
DE 102008029908 A1 12/2009
(Continued)

OTHER PUBLICATIONS

European Search Report for Counterpart EP17183415.3, dated Nov. 21, 2017.

*Primary Examiner* — Lucas A Stelling (57) ABSTRACT

A method and apparatus for operating a food waste recycling appliance includes a food waste recycling container, a condensate reservoir, a first fluid pathway fluidly coupling the food waste recycling chamber and the condensate reservoir, and a fan moving air from the food waste recycling chamber to the condensate reservoir along the first fluid pathway to define a first airflow.

14 Claims, 9 Drawing Sheets

(51) Int. Cl.
  *A61L 2/238*  (2006.01)
  *C02F 1/50*  (2006.01)
  *C05F 7/00*  (2006.01)
  *C05F 9/02*  (2006.01)
  *B65F 7/00*  (2006.01)
  *C05F 17/00*  (2006.01)
  *C05F 17/02*  (2006.01)
  *B02C 23/08*  (2006.01)
  *B02C 18/06*  (2006.01)
  *B02C 18/00*  (2006.01)
  *B02C 23/14*  (2006.01)

(52) U.S. Cl.
  CPC ...... *C02F 2303/20* (2013.01); *C02F 2307/12* (2013.01); *C05F 17/00* (2013.01); *C05F 17/02* (2013.01)

(56) References Cited

U.S. PATENT DOCUMENTS

| | | | |
|---|---|---|---|
| 5,307,650 A | 5/1994 | Mertz | |
| 5,507,108 A | 4/1996 | Bruggink et al. | |
| 5,587,320 A * | 12/1996 | Shindo | C05F 17/00 435/290.1 |
| 5,976,364 A | 11/1999 | Williams | |
| 6,120,686 A | 9/2000 | Bilz | |
| 6,303,039 B1 | 10/2001 | Back et al. | |
| 6,395,168 B1 * | 5/2002 | Acernese | C02F 1/50 210/198.1 |
| 6,946,196 B2 | 9/2005 | Foss | |
| 7,497,953 B2 | 3/2009 | Dart et al. | |
| 2005/0112339 A1 | 5/2005 | Sandel et al. | |
| 2006/0254626 A1 * | 11/2006 | Botts | A47L 15/0055 134/110 |
| 2008/0035769 A1 | 2/2008 | Manu | |
| 2008/0248075 A1 * | 10/2008 | Brambilla | A47L 15/4236 424/411 |
| 2012/0145198 A1 * | 6/2012 | Brockman | A61L 2/183 134/22.1 |
| 2013/0203849 A1 | 8/2013 | Ben Yehuda | |

FOREIGN PATENT DOCUMENTS

| | | |
|---|---|---|
| EP | 0676385 A2 | 10/1995 |
| GB | 2421946 A | 7/2006 |
| SE | 507250 C2 | 5/1998 |
| WO | 0056371 A1 | 9/2000 |
| WO | 2015186898 A1 | 12/2015 |

* cited by examiner

METHOD AND APPARATUS FOR PREVENTING MOLD GROWTH IN THE RESERVOIR OF A FOOD WASTE RECYCLING APPLIANCE

BACKGROUND

Food waste recycling appliances are known to implement a food waste recycling cycle for, at least in part, biologically and chemically decomposing organic material, such as food waste, for use as a fertilizer and soil amendment. The food waste recycling cycle can be implemented in a food waste recycling bin by providing water, heat and aeration to the refuse, and can require a period of time for completion. Food waste recycling appliances usually require a large floor space or a large volume for installation. Further, some food waste recycling appliances can be a batch type device, therefore cannot be effective in recycling food waste in a continuous way. The moisture released from the added food waste condenses into the reservoir of the food waste recycling appliance, where it remains relatively stagnant until the reservoir is periodically emptied.

BRIEF SUMMARY

In one aspect, an appliance includes a housing defining an interior, a water reservoir disposed in the interior of the housing for holding water used in an operation of the appliance; and a plurality of scrubs disposed in the water reservoir, each of the plurality of scrubs having a matrix of members in three dimensions, each member having a surface of exposed copper, wherein the copper inhibits growth of life forms in water in the reservoir.

In another aspect, a method of treating a water reservoir in an appliance is described, wherein the water reservoir has an inlet to enable water to be added to the reservoir. The method includes disposing a plurality of scrubs in the water reservoir, each of the plurality of scrubs having a matrix of members in three dimensions, each member having a surface of exposed copper; and maintaining water in the water reservoir with the plurality of scrubs, wherein the copper inhibits growth of life forms in water in the reservoir, and each of the plurality of scrubs is configured to not block the drain.

DETAILED DESCRIPTION

Figure 1:
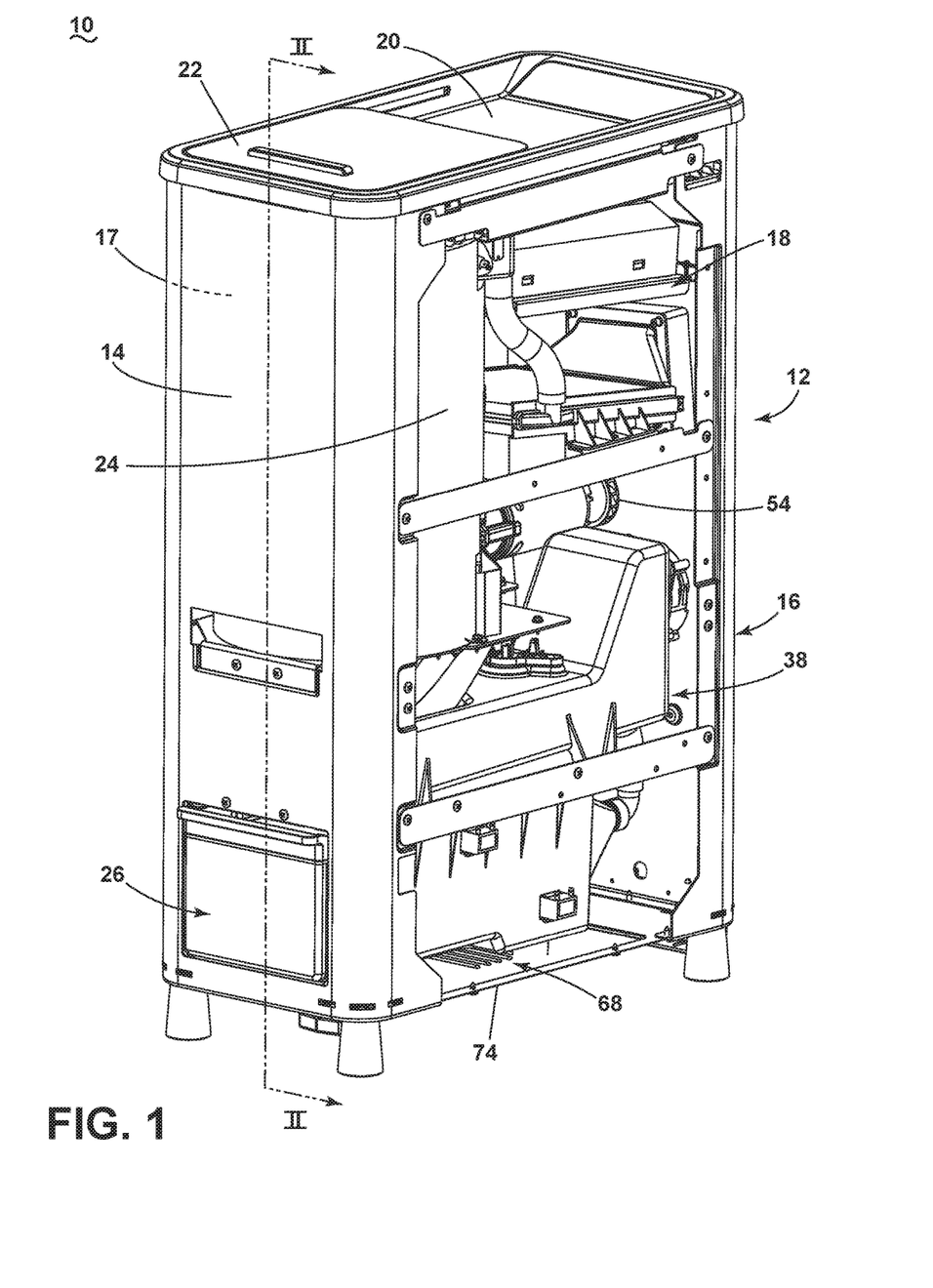
FIG. 1 is an isometric view of a food waste recycling appliance according to the inventive concept with a side panel removed, so as to better view the interior components.

FIG. 1 illustrates a perspective view of a food waste recycling appliance 10 for transforming organic material by way of a food waste recycling cycle of operation. While a "food waste recycling appliance" is described, embodiments of the invention can be equally applicable for similar devices, such as biological waste digesters. The food waste recycling appliance 10 can include a housing 12 having a front wall 14 spaced from a back wall 16, a pair of side walls 17, and a controller 18 located within the housing 12. One of the side walls 17 has been removed from FIG. 1 as shown to provide a better view of the components set in the interior of the appliance.

A top wall 20 can enclose the housing 12 at the top of the front wall 14, back wall 16, and the pair of side walls 17. The housing 12 can be any structure for enclosing, supporting and protecting the electrical and mechanical components of the food waste recycling appliance 10 including, but not limited to a cabinet and a frame.

The top wall 20 can include a cover 22 slidably mounted to a portion of the top wall 20 for sliding movement between open or closed positions to enable access to interior components of the food waste recycling appliance 10. The cover 22 can be any barrier that provides selective access for inputting organic material into the food waste recycling appliance 10, including, but not limited to a hingedly, slidably or removably mounted door, drawer, panel or lid. While shown in FIG. 1 as coupled to the top wall 20, the cover 22 can be mounted to any exterior wall enclosing the housing 12 including, but not limited to the front wall 14. The top wall 20, as well as the remainder of the housing 12, can be formed of any material suitable for construction of the housing structure including, but not limited to metal such as steel or steel alloy, plastic, composite materials such as a hardened polymer composite material and combinations thereof. Some models of food waste recycling appliances 10 can include decorative panels that can be mounted on the housing 12 or one or more walls.

When in the open position, the cover 22 provides access to the interior of the housing 12. In the open position, the cover can further expose any element of the food waste recycling appliance 10 interior of the housing 12, including but not limited to one or more water fill inlets for supplying water to the food waste recycling appliance 10 and one or more enzyme dispenser inlets. A food waste recycling bin 24 is provided within the housing 12. The food waste recycling bin 24 can be disposed beneath the cover 22 such that the cover provides selective access to the food waste recycling bin 24 as the cover is opened/closed.

An access drawer 26 is provided and slides in or out through an opening in the front wall 14. The access drawer 26 is a drawer slidably mounted to the housing 12 on a horizontal axis for movement between open and closed positions. It will be understood, however, that access to the interior of the food waste recycling appliance 10 via the front wall 14 can be provided in other ways, including but not limited to, a door pivotally connected to the front wall 14. The access drawer can be detachably mounted to an internal side of the housing 12 and is accessible from outside the housing 12. The access drawer 26 can be removable from the interior of the housing 12 so that the contents thereof can be discharged at will by a user, as for example, by dumping the contents of the drawer 26 onto a garden.

Figure 2:
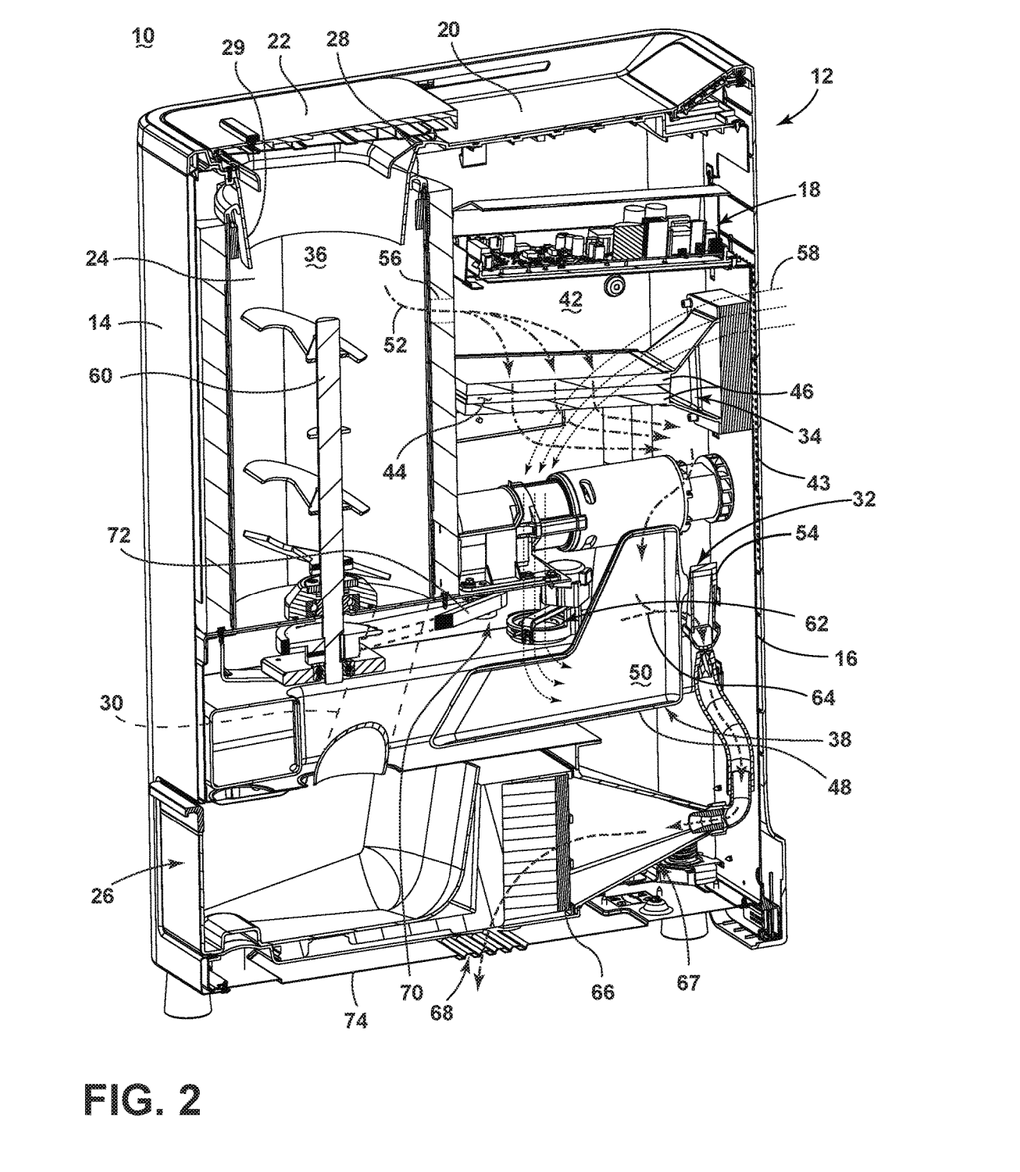
FIG. 2 is a cross sectional view of the food waste recycling appliance of FIG. 1 along line II-II'.
Figure 3:
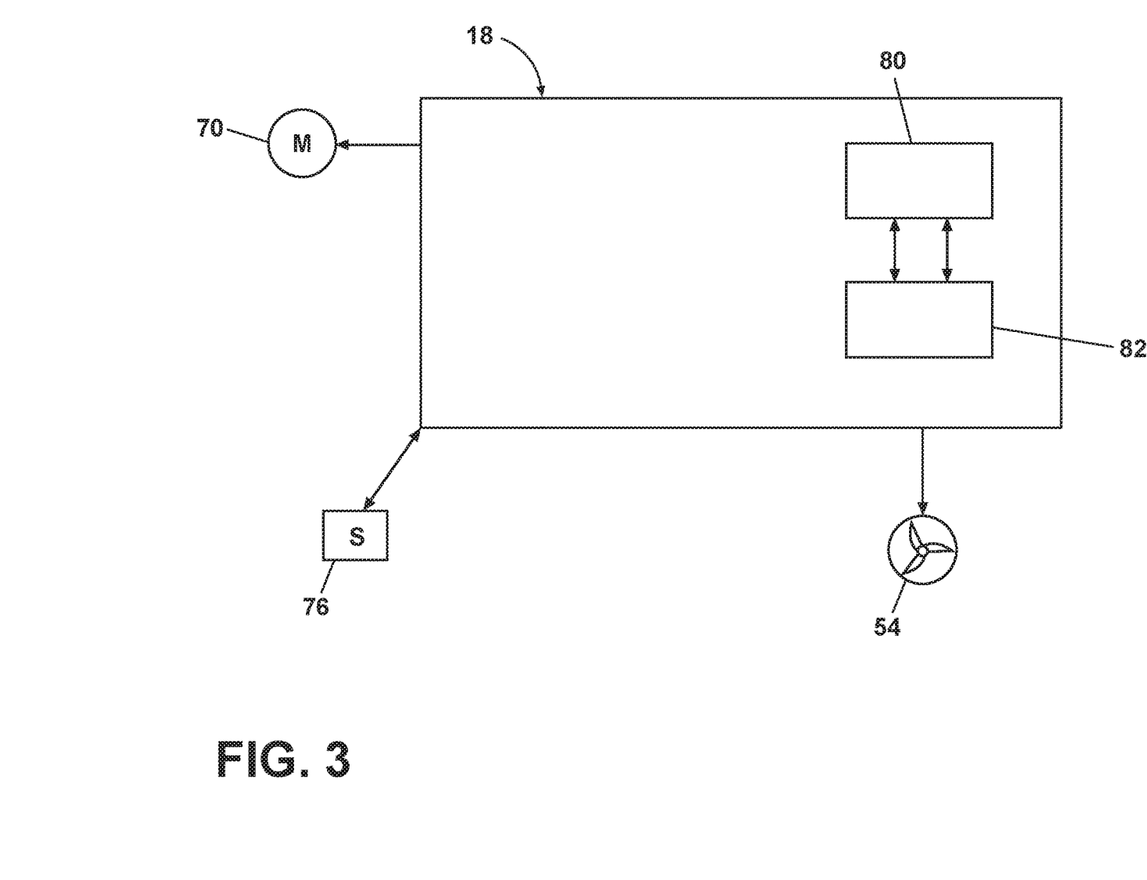
FIG. 3 is a schematic diagram of a control system of the food waste recycling appliance according to the inventive concept.

FIG. 2 illustrates a cross-sectional view of the food waste recycling appliance 10 of FIG. 1. The food waste recycling bin 24 can be fixedly or removable mounted to the housing 12. The food waste recycling bin 24 can define a chamber 36 configured to receive organic material from outside of the food waste recycling appliance 10, either directly or indirectly. The food waste recycling bin 24 can include an open top 28 of the bin 24 for receiving refuse through the top wall 20 of food waste recycling appliance 10. As shown, the top wall 20 can also include a funnel 29 located to align with the open top 28 of the food waste recycling bin 24 such that refuse placed in through the top wall 20 into the funnel 29 is guided into the open top 28 of the food waste recycler bin 24.

The housing 12 can also include a porous wall 43, shown as a portion of the back wall 16, wherein the porous wall 43 is configured to allow ambient air to flow into or out of the interior 42 of the housing 12. While the portion of the back wall 16 has been illustrated having the porous wall, embodiments of the disclosure can include a porous portion of one or more of any of the previously described walls 14, 17, 20.

As shown, a conduit 30 can extend from the food waste recycler bin 24, such as from a lower portion of the food waste recycler bin 24, toward the access drawer 26. Embodiments of the disclosure can optionally include a transfer mechanism disposed inside the conduit 30 capable of assisting the transfer of material from the food waste recycler bin 24 to the access drawer 26. Examples of a transfer mechanism can include, but are not limited to, a rotatable auger, a conveyor, a gravitational chute, and the like.

A reducing mechanism 60 can be provided adjacent or within the food waste recycler bin 24. The reducing mechanism 60 can be in the form of a mixer, an auger, a grinding wheel, a grinding blade, any chopping mechanism, or any like device or combination thereof that grinds, shears chops, mixes, breaks, or otherwise reduces the particle sizes of refuse by the operation of the reducing mechanism 60 or uniformly mixing refuse with water, air or enzymes that can be introduced in the food waste recycler bin 24 for at least one of chemically or biologically transforming the refuse.

A motor 70 can be provided inside the cabinet 12 and can be operably coupled to the reducing mechanism 60 to operate, rotate, toggle, or actuate the reducing mechanism 60. As shown, the motor 70 can be operatively coupled with the reducing mechanism 60 by way of a belt or pulley system 72. The motor 70 can be a brushless permanent magnet (BPM) motor. Alternately, other motors such as an induction motor or a permanent split capacitor (PSC) motor can also be used. The motor 70 can be configured to operate the reducing mechanism 60 at different speeds during the cycle of operation to facilitate the reducing or mixing of refuse in the interior of the food waste recycler bin 24 or the access drawer 26.

The food waste recycling appliance 10 further includes a heat exchanger 34, a water reservoir, including but not limited to a condensate reservoir 38, a filter 66, and an air supply system 32, all of which are located within an interior 42 of the housing 12.

The heat exchanger 34 can include a fluid pathway 44 defined between a set of heat conducting elements 46, such as plates, configured such that the heat conducting elements 46 absorb, conduct, pull, or otherwise remove at least a portion of heat from air traversing the fluid pathway 44. At least a portion of the heat removed from the air traversing the fluid pathway 44 can be dissipated, conducted, or radiated into the air occupying the interior 42 of the housing 12. Embodiments of the disclosure can include a heat exchanger 34 having a fluid pathway 44 sealed, closed, or isolated from the interior 42 of the housing 12, such that heat can be removed or transferred out of the fluid pathway 44 without intermixing fluid traversing the pathway 44 with the interior 42.

The condensate reservoir 38 can include a body 48 defining an interior 50 for holding liquid, such as water, and can be fluidly coupled downstream from the fluid pathway 44 of the heat exchanger 34. The condensate reservoir 38 can also include a second fluid coupling, separate from the fluid coupling with the fluid pathway 44 such as a controllable valve 62, configured to provide access to the interior 50 of the reservoir 38. The controllable valve 62 can be communicatively coupled with the controller 18, and can be configured to at least partially open, partially close, or actuate in response to instructions provided by the controller 18. In this sense, the controller 18 can operate the controllable valve 62 to provide selective access to the interior 50 of the reservoir 38. While a controllable valve 62 is described, embodiments of the disclosure can include a fixed opening or fixed port providing uncontrollable access to the interior 50 of the reservoir 38.

Figure 4:
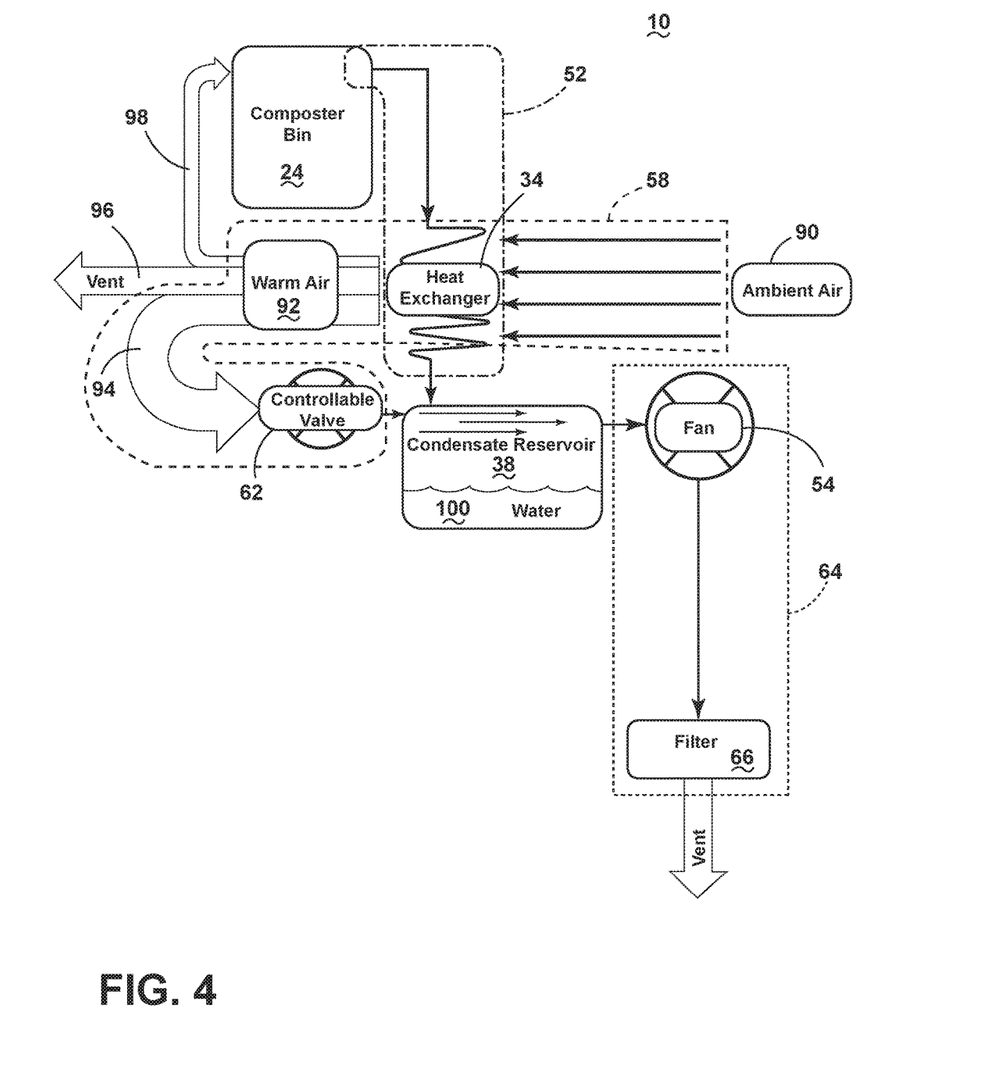
FIG. 4 is a schematic diagram illustrating an operation of the ventilation system of the food waste recycling appliance.

The air supply system 32 provides air flow for the food waste recycling appliance 10. The air supply system 32 can include a fan 54 or vacuum pump for supplying, drawing, receiving, or forcing air, for example, through a first fluid pathway (illustrated as arrows 52). The first fluid pathway 52 can include, but is not limited to, a pathway defined to transmit the food waste recycling air from the chamber 36 of the food waste recycler bin 24, for example through an opening 56 in the bin 24 wall, through the fluid pathway 44 of the heat exchanger 34, and into the interior 50 of the condensate reservoir 38. The first fluid pathway 52 can include tubing, closed channels, ducting, or the like to define sealed or contained pathway 52, since the food waste recycling air delivered may include undesirable odors or smells emitted as byproducts of the food waste recycling cycle of operation.

The air supply system 32 can also include a fan 54 or vacuum pump for supplying drawing, receiving, or forcing air, for example through a second fluid pathway (illustrated as arrows 58). The second fluid pathway 58 can include, but is not limited to, a pathway defined to transmit ambient air from the interior 52 of the food waste recycling appliance 10 into the interior 50 condensate reservoir 38, for example, via the controllable valve 62. In one embodiment, the ambient air can be drawn from ambient air external to the housing 12, such as through the porous wall 43, into the interior 42 of the food waste recycling appliance 10. The ambient air located within the interior 42 of the food waste recycling appliance 10 can also include a portion of air heated by way of the heat exchanger 34 dissipating, conducting, or radiating heat to the interior 42 of the housing 12, as explained above. The fan 54 configured to draw, receive, or force air along the first fluid pathway 52 can be the same fan 54 configured to draw, receive, or force air along the second fluid pathway 58. In this sense, the controllable valve 62 can further be utilized to control the drawing of air along the first fluid pathway 52. For example, if the fan 54 draws a predetermined amount of airflow from the interior 50 of the condensate reservoir 38, the opening or closing of the controllable valve 62 can have the technical effect of redistributing or rebalancing the draw of the airflow from the respective first fluid pathway 52 and the second fluid pathway 58. For instance, restricting the second fluid pathway 58 by way of closing the controllable valve 62 produces additional airflow drawn from the first fluid pathway 52, whereas opening the controllable valve 62 reduces airflow drawn from the first fluid pathway 52. Alternative embodiments can include configurations wherein each fluid pathway 52, 58 as a different source, such as a set of fans 54, for supplying airflow in each respective pathway 52, 58. As used herein, the fan 54 or vacuum pump can be configured to create negative pressure to draw air along at least one of the first fluid pathway 52 or second fluid pathway 58.

The food waste recycling appliance 10 can additionally include a third fluid pathway (illustrated as arrows 64) configured to remove or vent air in the interior 50 of the condensate reservoir 38 to the outside of, or external to the housing 12. For example, the third fluid pathway 64 can include a pathway sealed, closed, or isolated from the interior 42 of the housing 12, and configured to direct airflow through, for example, a filter 66 prior to venting the airflow through an air outlet 68, which is illustrated on a bottom wall 74 of the housing 12. The filter 66 can include a diffuser 67, or can be configured to filter or remove undesirable elements from the airflow downstream of the condensate reservoir 38. Undesirable elements can include, but are not limited to, odors or microbes originating from the food waste recycling cycle of operation. Examples of filter 66 materials can include, but are not limited to, charcoal, previously at least partially chemically or biologically degraded material, a biofilter material, or activated carbon. Additional filters 66 can include utilizing ultraviolet lighting or ozone, for example, via an ozone generator, to provide at least a portion of the filtering of undesirable elements from the airflow downstream of the condensate reservoir 38. As a variant, another mode of emptying the water 100 from the condensate reservoir may employ the use of a drain 120, which may be regulated with a valve 122.

As the Food Waste Recycling air in the first fluid pathway 52 moves across the heat conducting plates 46 of heat exchanger 34, the temperature of the Food Waste Recycling air can be cooled or reduced by 20 to 30 degree Celsius. The reduction in temperature of the Food Waste Recycling air, in turn, causes condensation, or excess moisture or water vapor, to fall out of or condense from the air, gathering as liquid. The liquid condensation can also flow through the first fluid pathway 52 exiting the heat exchanger 34, and gather in the condensate reservoir 38, illustrated as water 100. While "water" is described, embodiments of the disclosure can include examples wherein the water 100 is not pure water, and can include amounts of soil amendment or fertilizer, odor and bacteria. The cooled Food Waste Recycling air traverses the portion of the first fluid pathway 52 downstream from the heat exchanger 34, and ultimately enters the condensate reservoir 38. In this sense, a first airflow passes from the Food Waste Recycling bin 24, through the heat exchanger 34 where heat is removed from the first airflow and condensation forms, and the first airflow and condensation are each provided to the condensate reservoir 38. Additionally, at least a portion of the first fluid pathway 52 can include a liquid pathway configured to deliver the condensate or water 100 to the reservoir 38.

Figure 5:
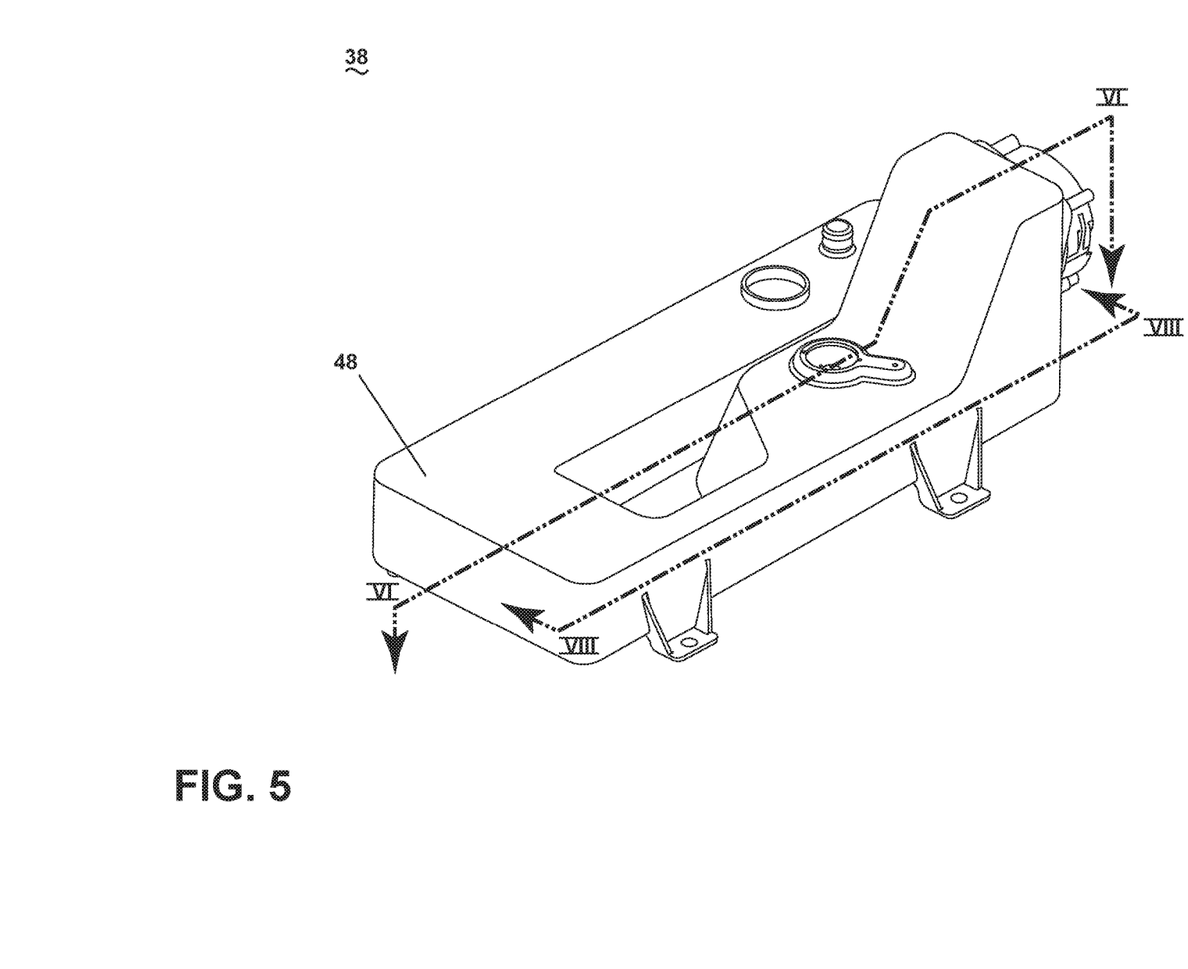
FIG. 5 is an isometric view of the reservoir of the food waste recycling appliance of FIG. 1.
Figure 6:
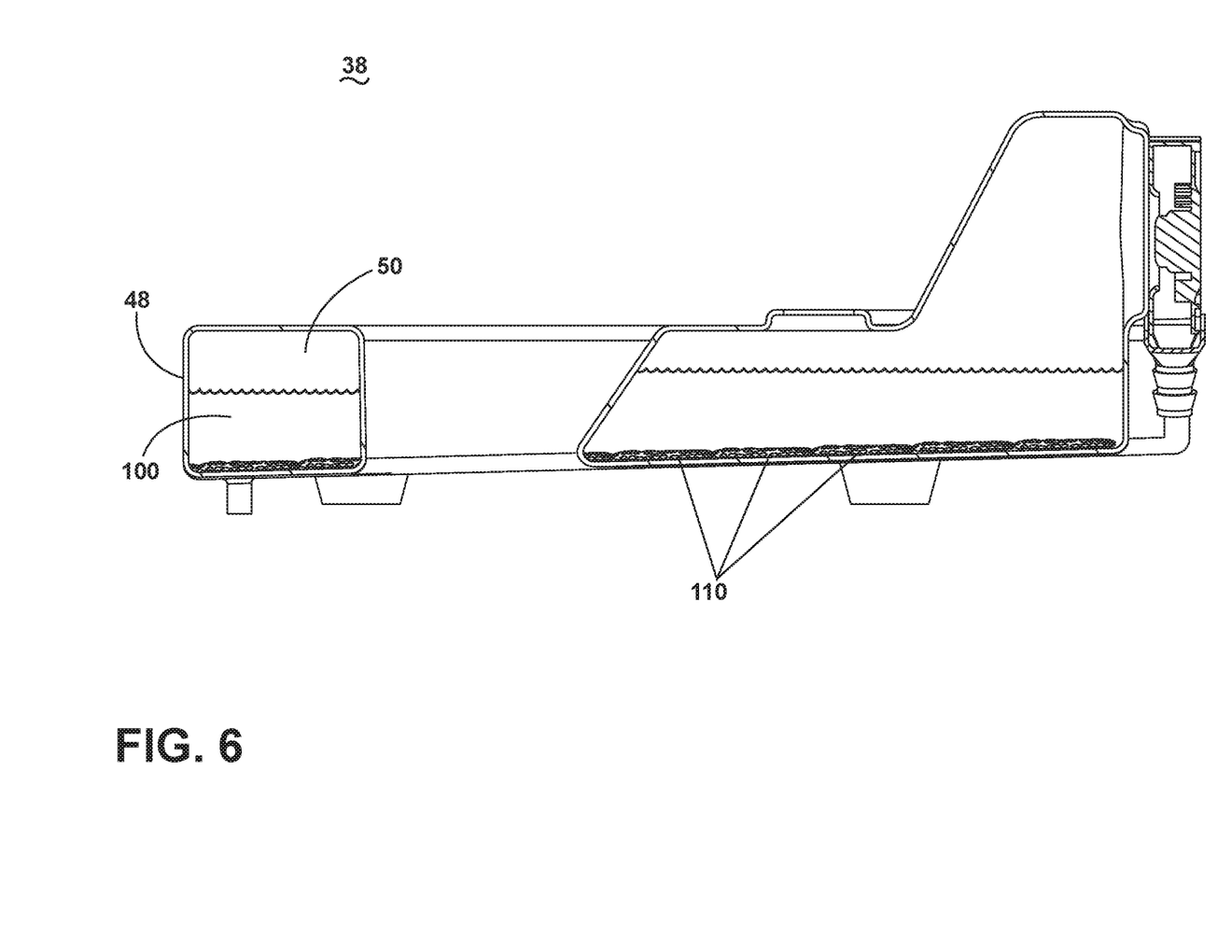
FIG. 6 is the cross sectional view of the reservoir of FIG. 5 along line VI-VI'.
Figure 7:
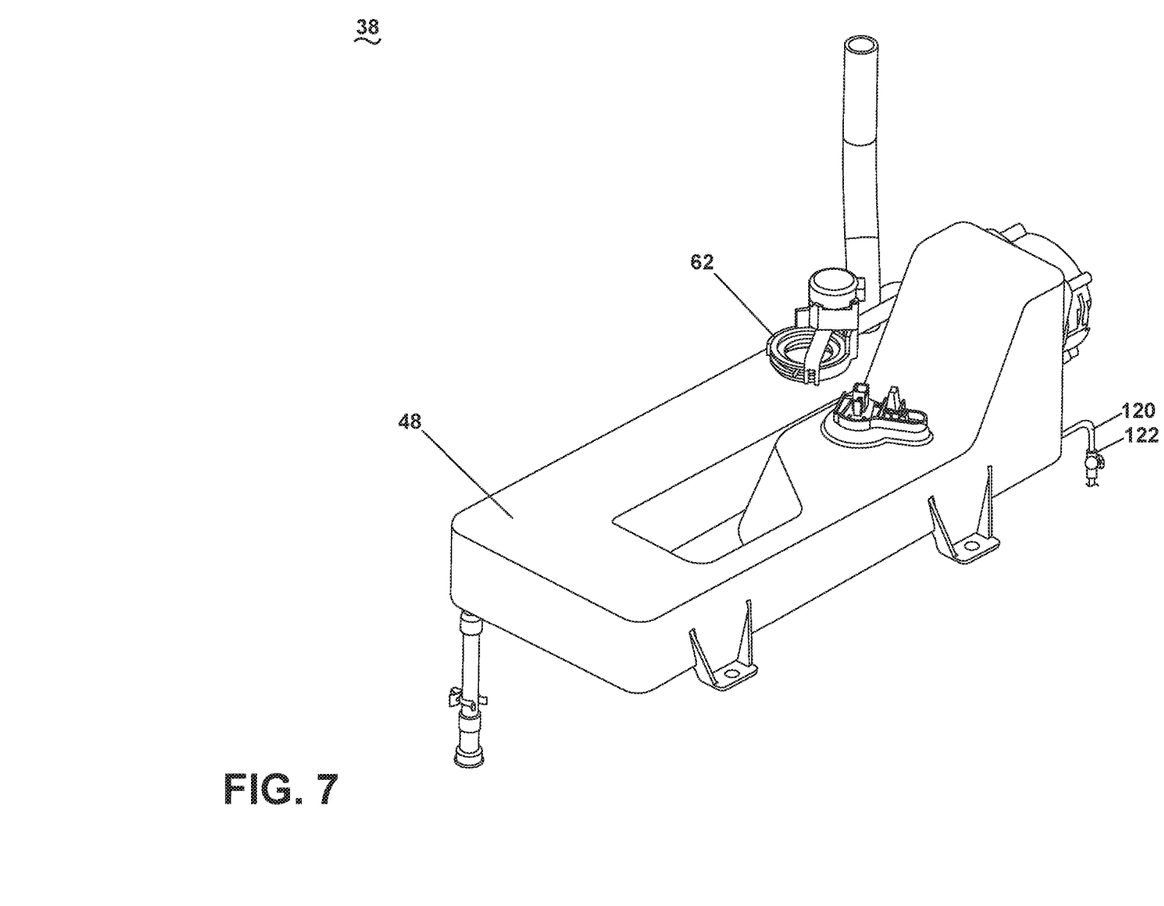
FIG. 7 is an isometric view of the reservoir of the food waste recycling appliance of FIG. 1, in the context of its various attachments that couple it to the rest of the food waste recycling appliance.
Figure 8:
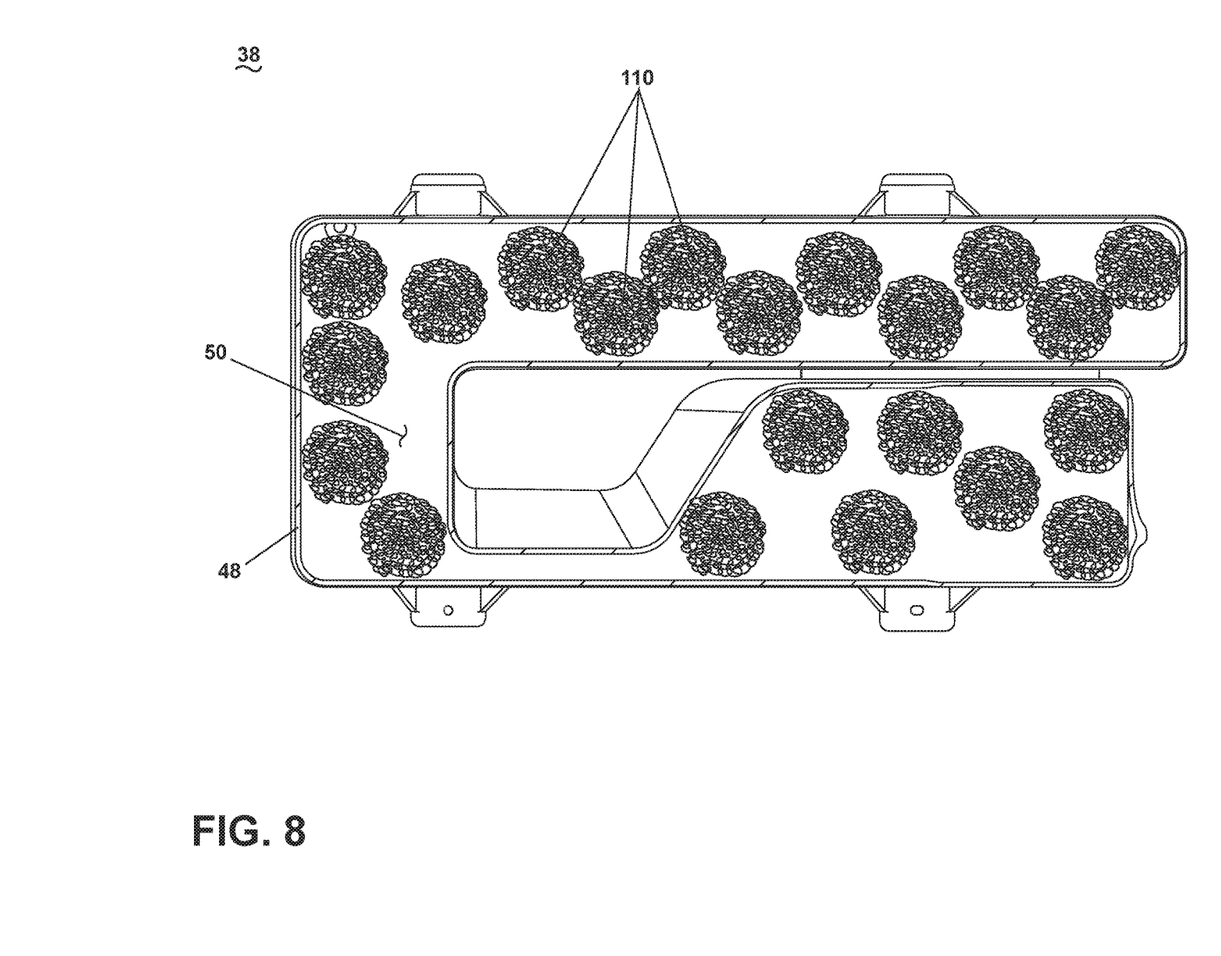
FIG. 8 is the cross sectional view of the reservoir of FIG. 5 along line VIII-VIII'.

The water 100 that collects in the interior 50 of the condensate reservoir 38 is exposed to a plurality of copper scrubs 110 disposed in the condensate reservoir 38. Each of the copper scrubs 110 comprises a plurality of copper filaments, which are intertwined with each other to form a matrix in three dimensions. The size and shape of the scrubs 110 is such that they do not block a drain 120 for the water reservoir. In a non-limiting embodiment, the scrubs 110 can be substantially cylindrically shaped, with a diameter of each larger than the height, enabling them to lay on a bottom of the condensate reservoir 38.

The size and shape of the copper scrubs 110 enables ease in draining the reservoir 38 either continuously or intermittently without the copper scrubs blocking the drain 120. The fact that the copper scrubs 110 are composed of thin filaments of copper enables a much larger surface area of the elemental copper to be exposed to the water 100, thereby improving the biocidal action of a given mass of copper used. Thus, it would be deemed for it to be feasible to be able to use a much smaller mass of copper per unit mass of water, than if the copper were made available to contact the water in the physical form of a solid cylinder. The elemental copper in the scrubs 110 inhibits the growth of life forms in the accumulated water 100. Thus the stagnant water 100 can be allowed to accumulate for a longer period of time, without risk of growth of life forms in the condensate reservoir 38.

While the scrubs 110 described here comprise filaments of essentially pure elemental copper, it should be noted that similar efficacy in biocidal activity can be obtained by using copper plated scrubs, as the exposed surface of the scrub filaments would still comprise elemental copper.

Figure 9:
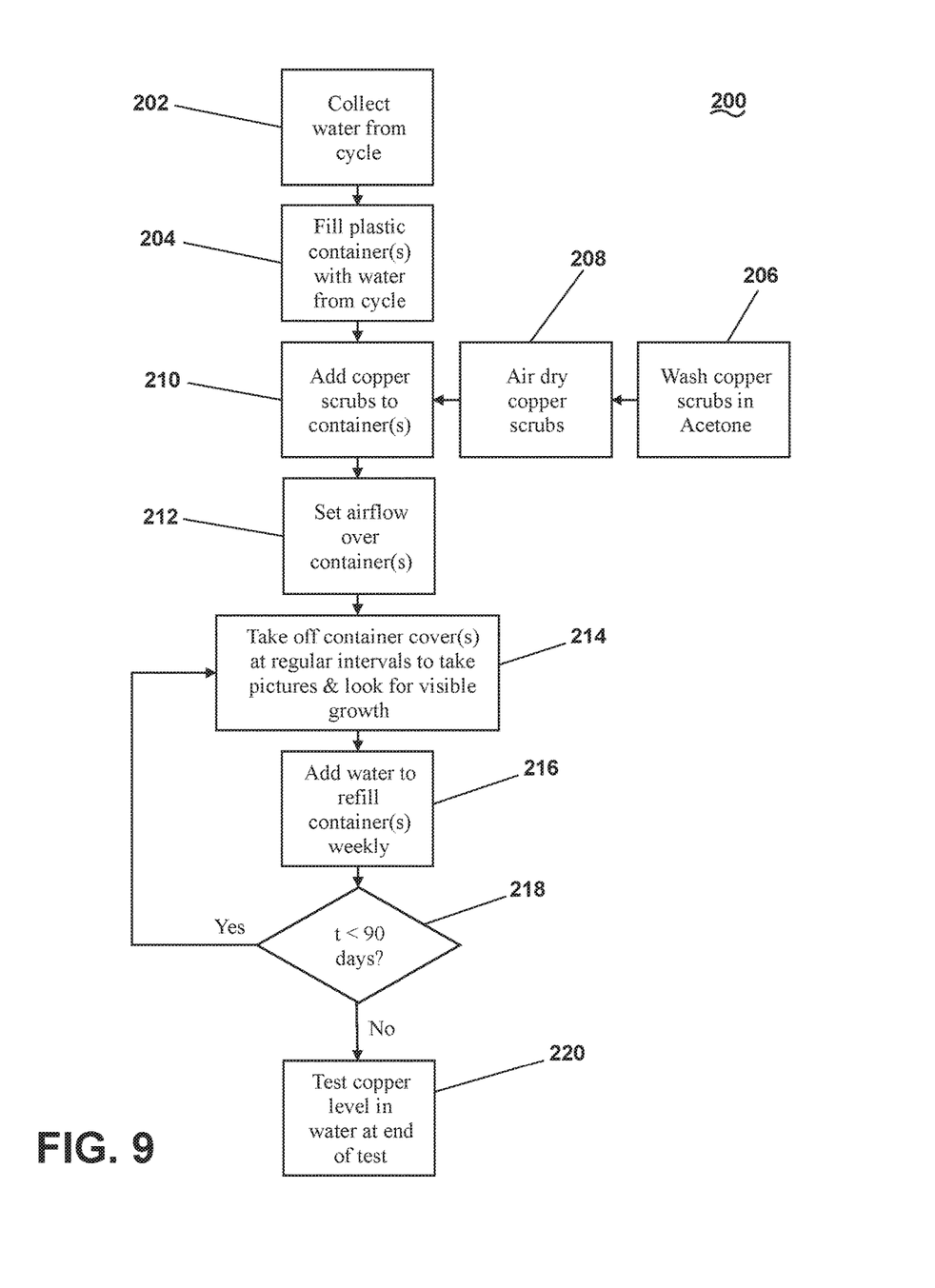
FIG. 9 is the flowchart of an experimental protocol used to replicate a function of the food waste recycling appliance.

FIG. 9 describes a flowchart of an experimental protocol 200 used to generate the data in TABLE 2 and TABLE 3. The food waste recycling cycle of operation is conducted using the food items listed in TABLE 1 as the raw material. The moisture generated from the food waste recycling cycle of operation is collected at step 202. At step 204, one or more plastic containers are filled to a predetermined volume with the water collected from step 202. Separately, a predetermined number of copper scrubs are cleaned in acetone to remove any dirt or undesirable substances on the surface of the filaments of the scrubs, at step 206. Subsequently, the copper scrubs are air dried to evaporate the acetone at step 208. At step 210, the copper scrubs are added to the plastic containers. At step 212, the air flow rate over the surface of the water in the containers is set to a predetermined number, measured in Cubic Feet per Minute (CFM). Subsequently, the containers are closed and left undisturbed. At step 214, the container covers are taken off at regular intervals and photographs are taken to record the presence or absence of any signs of visible growth of life forms. Subsequently, at step 216, sufficient water is added to the containers to bring them back up to the original fill level at step 204. At this juncture, at step 218, if 90 days have passed since the start of the experimental run, the experimental run is concluded and the final copper level in the water is measured at step 220. If 90 days have not yet passed, steps 214 and 216 are repeated at regular predetermined intervals until 90 days have passed and the experimental run can be concluded.

TABLE 1

| Food Item | % by weight | Weight added (g) |
| --- | --- | --- |
| Sliced white bread | 17.1 | 599.8 |
| Sliced American cheese | 3.8 | 133.9 |
| Head lettuce | 9.5 | 331.9 |
| Broccoli | 9.5 | 331.9 |
| Carrots | 9.5 | 331.9 |
| Apples | 9.5 | 331.9 |
| Bananas | 9.5 | 331.9 |

TABLE 1-continued

| Food Item | % by weight | Weight added (g) |
|---|---|---|
| Cottage cheese (large curd) | 13.3 | 465.9 |
| Canned chicken breast | 9.5 | 331.9 |
| Canned tuna | 3.8 | 133.9 |
| Coffee | 5.0 | 174.7 |
| Coir | Fixed | 292.0 |
| Baking soda | Dose | 40.0 |
| Total food load weight (g) | | 3500.0 |

TABLE 2 and TABLE 3 present a tabular description of two experimental runs done to validate the concept under the experimental procedure described above in two sealable plastic containers. TABLE 2 had no copper scrubs and TABLE 3 had 123.14 grams of copper scrubs.

TABLE 2

(Without Copper)

| | | |
|---|---|---|
| Fan CFM | 0.36 | cfm |
| Voltage | 4 | V |
| Water initial | 1067.550 | g |
| Scrub weight | 0.000 | g |
| Container weight | 722.670 | g |
| Tape weight | 15.320 | g |
| Water add | 1009.560 | g |

| Day | Growth (yes/no) | |
|---|---|---|
| 0 | N/A | |
| 5 | no | |
| 5 | no | added water |
| 6 | no | |
| 7 | no | |
| 8 | yes | |
| 9 | yes | |
| 12 | yes | added 1500 ml of water |
| 13 | yes | |
| 14 | yes | |
| 15 | yes | |
| 16 | yes | |
| 21 | yes | |
| 33 | yes | |
| 34 | yes | |

TABLE 3

(With Copper)

| | | |
|---|---|---|
| Fan CFM | 0.36 | cfm |
| Voltage | 4 | V |
| Water initial | 1031.460 | g |
| Scrub weight | 123.140 | g |
| Container weight | 720.550 | g |
| Tape weight | 13.270 | g |
| Water add | 1008.340 | g |

| Day | Growth (yes/no) | |
|---|---|---|
| 0 | N/A | |
| 5 | no | |
| 5 | no | added water |
| 6 | no | |
| 7 | no | |
| 8 | no | |
| 9 | no | |
| 12 | no | added 1500 ml of water |
| 13 | no | |
| 14 | no | |

TABLE 3-continued (With Copper)

| | |
|---|---|
| 15 | no |
| 16 | no |
| 21 | no |
| 33 | no |
| 34 | no |

The specific copper scrubs used in the above experiments were Chore Boy copper scrubs bought from amazon.com and were substantially cylindrical in shape and had an average diameter of 80.4 mm, an average height of 31.1 mm and an average weight of 12.2 grams over a sample size of 108 scrubs. The scrubs were found to have an elemental copper content of 99.9% by weight over a sample size of 2 scrubs.

While the above disclosure describes the use of copper scrubs which manifest biocidal activity in the reservoir of a food waste recycling appliance, other biocidal agents may also be used, including but not limited to salt. In the case of using salt, given the high solubility of salt in aqueous solutions, the salt would dissolve completely, thereby not causing a concern with respect to blocking the drain 120.

To the extent not already described, the different features and structures of the various embodiments can be used in combination with each other as desired. That one feature cannot be illustrated in all of the embodiments is not meant to be construed that it cannot be, but is done for brevity of description. Thus, the various features of the different embodiments can be mixed and matched as desired to form new embodiments, whether or not the new embodiments are expressly described. Moreover, while "a set of" various elements have been described, it will be understood that "a set" can include any number of the respective elements, including only one element. Combinations or permutations of features described herein are covered by this disclosure.

This written description uses examples to disclose embodiments of the invention, and also to enable any person skilled in the art to practice embodiments of the invention, including making and using any devices or systems and performing any incorporated methods. The patentable scope of the invention is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A food waste recycling appliance comprising:
a housing defining an interior;
a recycling chamber located within the interior and configured to receive organic material for recycling;
a reducing mechanism provided within the recycling chamber and configured to mix the organic material with air;
a container configured to receive the recycled organic material from the recycling chamber;
a condensate reservoir located within the interior of the housing and fluidly coupled to the recycling chamber; and
a plurality of biocidal agents disposed in the condensate reservoir, each of the plurality of biocidal agents having a plurality of filaments intertwined with each other to form a matrix in three dimensions, wherein each of the plurality of filaments comprises a surface of exposed copper.

2. The food waste recycling appliance of claim 1 wherein each of the plurality of filaments are copper wires.

3. The food waste recycling appliance of claim 1 wherein each of the plurality of filaments are covered by copper.

4. The food waste recycling appliance of claim 1 further comprising an air flow conduit in communication with the condensate reservoir.

5. The food waste recycling appliance of claim 1 wherein each of the plurality of biocidal agents is substantially cylindrical and has a diameter of about 80.4 mm and a height of about 31.1 mm.

6. The food waste recycling appliance of claim 1 wherein each of the plurality of biocidal agents has about 99.9 percent by weight of elemental copper.

7. The food waste recycling appliance of claim 1 wherein the condensate reservoir has a drain, and each of the plurality of biocidal agents is dimensioned to avoid blocking the drain.

8. A method of treating liquid in a condensate reservoir in a food waste recycling appliance, the method comprising:
operating a reducing mechanism within a chamber of the food waste recycling appliance containing organic material to generate moisture;
flowing the moisture from the chamber;
converting the moisture to condensate and storing the condensate within the condensate reservoir;
exposing a plurality of biocidal agents to the condensate within the condensate reservoir, each of the plurality of biocidal agents having a plurality of filaments intertwined with each other to form a matrix in three dimensions, wherein each of the plurality of filaments comprises a surface of exposed copper; and
maintaining liquid in the condensate reservoir with the plurality of biocidal agents, wherein the copper inhibits growth of life forms in liquid in the reservoir.

9. The method of claim 8 wherein each of the plurality of filaments are copper wires.

10. The method of claim 8 wherein each of the plurality of filaments are covered by copper.

11. The method of claim 8 further comprising flowing air into the water-condensate reservoir.

12. The method of claim 8 wherein each of the plurality of biocidal agents is substantially cylindrical and has a diameter of about 80.44 mm and a height of about 31.1 mm.

13. The method of claim 8 wherein each of the plurality of biocidal agents has about 99.9 percent by weight of elemental copper.

14. The method of claim 8 wherein the condensate reservoir has a drain, and each of the plurality of biocidal agents is dimensioned to avoid blocking the drain.

* * * * *